United States Patent
Burton et al.

[11] Patent Number: 6,142,953
[45] Date of Patent: Nov. 7, 2000

[54] RESPIRATORY INDUCTIVE PLETHYSMOGRAPHY BAND TRANSDUCER

[75] Inventors: David Burton, Camberwell; Jiang Hong Tan, Mount Waverly, both of Australia

[73] Assignee: Compumedics Sleep Pty Ltd, Australia

[21] Appl. No.: 09/349,855

[22] Filed: Jul. 8, 1999

[51] Int. Cl.$^7$ ..................................................... A61B 5/08
[52] U.S. Cl. ..................... 600/534; 600/535; 324/207.22
[58] Field of Search ................................... 600/534–535; 324/207.16, 207.22

[56] References Cited

U.S. PATENT DOCUMENTS

| 4,308,872 | 1/1982 | Watson | 128/725 |
| 5,131,399 | 7/1992 | Sciarra | 128/671 |
| 5,301,678 | 4/1994 | Watson et al. | 128/721 |
| 5,331,968 | 7/1994 | Williams et al. | 600/535 X |
| 5,611,349 | 3/1997 | Halleck et al. | 600/534 |
| 5,913,830 | 6/1999 | Miles | 600/535 |

*Primary Examiner*—Cary O'Connor
*Assistant Examiner*—Ryan Carter
*Attorney, Agent, or Firm*—Nikolai, Mersereau & Dietz, P.A.

[57] ABSTRACT

A device for reliably and non-invasively measuring respiration rates and effort by encircling the patient's chest with a device having a large section of inelastic belt attached to a small section of elastic material. The elastic material having two magnetic tapes with wire windings thereon proximate each other with an insulation material therebetween. The wire windings are electrically connected to each other. The magnetic tapes have opposite ends attached to the elastic material such that when the elastic material expands and contracts the wire windings move relative to each. A toroidal transformer is connected to the wire windings. When a carrier signal is introduced to the transformer and the magnetic tapes move relative to each other on the elastic material when the patient breathes a mutual inductance in the wire windings modulates the carrier signal and thus measures the expansion and contraction of the patient's chest which is directly related to the patient's respiration rate. The electronics connected to the device for monitoring respiration also measures belt shifting for diameter changes during monitoring by measuring the central amplitude during a breath cycle and comparing the initial belt diameter conditions to later conditions. The electronics can then compensate for amplitude variations in the signal caused by belt shifting which may be confused with shallower breathing in uncompensated devices.

10 Claims, 2 Drawing Sheets

RESPIRATORY INDUCTIVE PLETHYSMOGRAPHY BAND TRANSDUCER

BACKGROUND OF THE INVENTION

1. Field of the Invention

The present invention relates to a device for measuring of expansion and contraction in general and particularly monitoring for the respiration of patients by moving coils producing a mutual induction for modulating a carrier signal.

2. Description of the Related Art

Many devices measure the respiration of patients. In one method a mask placed over the patient's mouth and nose measures flow rates of inhaled and exhaled breath. This is uncomfortable for the patient and requires a lot of cumbersome equipment.

Other methods of monitoring breathing include the measurement of thoracic impedance with the use of electrodes placed on the patient. However there are many electrical signals in the body from the heart and other muscles, which are picked up by such electrodes and interfere with the monitoring of the thoracic impedance.

Another method of monitoring a patient's breathing is by measuring the patient's torso to detect expansion and contraction, which is directly proportional to the volume and rate of inhaling and exhaling. There are many devices, which use this approach to monitoring a patient. Some devices use resistance strips which changes current as the strip is elongated, other methods use strain gages and still others use inductance coils which move relative to each other. For example U.S Pat. No. 5,131,399 to Sciarra provides for a respiration transducer with a pair of coiled wires wound side by side to provide mutual inductance.

The mutual inductance signals can be measured easier if the relative movement between the coiled wires is greater. Therefore a device is required which has a close proximity between the coils for high mutual inductance and yet provides for a. larger relative movement when the patient breathes.

A problem in the prior art is that the belts attached around the patient frequently slip or shift changing the diameter of the belt and thereby changing the signals received from the belt. A belt shift to a smaller diameter portion of the body may result in a signal with reduced amplitude, which may be confused with an indication that the patient's breathing is shallower.

SUMMARY OF THE INVENTION

The invention comprises two adjacent overlapping magnetic tapes wound with wires such that they form inductance coils with an insulating plate therebetween. There are two elastic strips one having the magnetic tapes attached such that the tapes overlap in the middle of their combined lengths and are attached to one of the elastic strips at the far ends of the magnetic strips. The elastic strips are sewn together and an inelastic cloth is attached to one elastic strip adjacent the magnetic tapes to limit the relative motion of the magnetic tapes so as to prevent excessive stretching which could damage the device. The two magnetic strips are wound with a wire, which connects the two windings for mutual inductance. The two magnetic strip windings are also connected to a toroidal transformer. A carrier signal may be used in connection with the toroidal transformer. When one strip moves relative to the other a mutual inductance is used to modulate the carrier signal and thereby measure the magnetic strips relative movement. An inelastic belt connected to the elastic strips is used to encircle the patient's chest. When the patient breaths the elastic strips expand and contract moving the magnetic strips relative to each other. The mutually induced signals are used to monitor a patient's respiration both for the amplitude of the breath indicating the effort level and for the rate or repetition of breathing. If the belt shifts position on the patient the diameter of the belt will change as will the amplitude of the signals received. A compensating signal is used to correct for shifts of the belts position resulting in a more accurate monitoring of the patient's respiration.

OBJECTS OF THE INVENTION

It is an object of the invention to provide accurate and reliable respiratory monitoring of a patient.

It is an object of the invention to provide accurate and reliable respiratory monitoring of a patient to detect the patent's breathing rate.

It is an object of the invention to provide accurate and reliable respiratory monitoring of a patient to detect the patent's breathing effort.

It is a further object of the invention to provide a non-invasive respiratory monitoring of a patient.

It is also an object of the invention to provide a mutual inductance signal from two closely spaced magnetic tapes having wire windings, which move relative to each other in conjunction with the respiration of a patient.

It is a still further object of the invention to provide a low cost, easy to use respiratory monitoring device.

It is an object of the invention to compensate for shifting diameters of the belt to provide a more accurate monitoring of respiration.

It is also an object of the invention to provide a device for measuring the expansion and contraction of objects in general.

Other objects, advantages and novel features of the present invention will become apparent from the following detailed description of the invention when considered in conjunction with the accompanying drawings.

DESCRIPTION OF THE PREFERRED EMBODIMENTS

Figure 1:
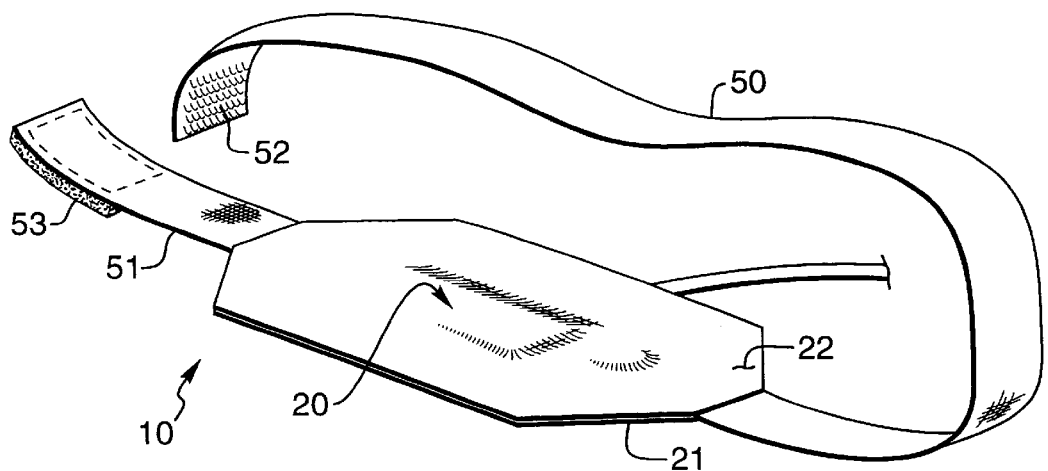
FIG. 1 is a perspective view of the Respiratory Inductive Plethysmography Band Transducer Belt.
Figure 2:
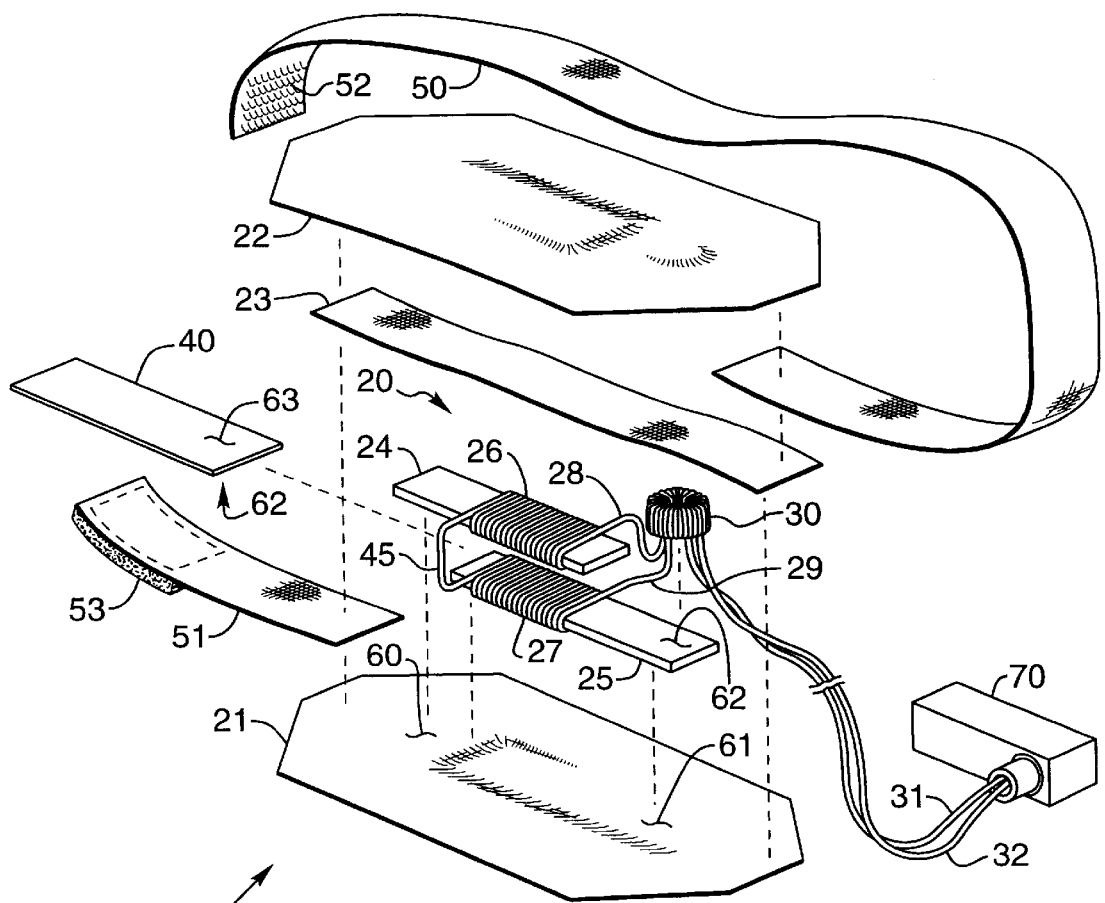
FIG. 2 is an exploded perspective view of the Respiratory Inductive Plethysmography Band Transducer sandwiched between elastic strips.

FIG. 1 shows a perspective view of the Respiratory Inductive Plethysmography Band Transducer Belt 10 for measuring the respiration rate and effort of a patient. The Respiratory Inductive Plethysmography Band Transducer 20 is attached to elastic strip 21. As FIG. 2 shows elastic strip 21 is also attached to elastic strip 22. Elastic strips 21 and 22 are attached to inelastic belt segments 50 and 51 which have mutually engageable fastener portions 52, 53.

Figure 3:
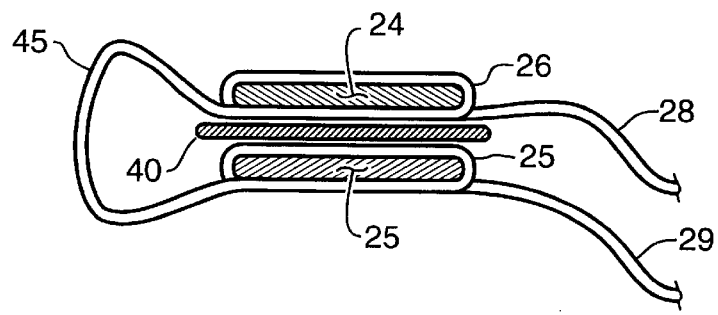
FIG. 3 is an end view of the magnetic strips and insulation plate.

FIG. 2 shows an exploded perspective view of the Respiratory Inductive Plethysmography Band Transducer 20 sandwiched between elastic strips 21 and 22. Magnetic tapes 24, 25 are proximate each other. Magnetic tape 24 has wire windings 26, and magnetic tape 25 has wire windings 27. The wire windings 26 and 27 are connected by wire 45. As more clearly shown in FIGS. 3 and 4, an insulation plate 40 is placed between magnetic tapes 24, 25 to insulate them and wire windings 26, 27 from each other.

Figure 4:
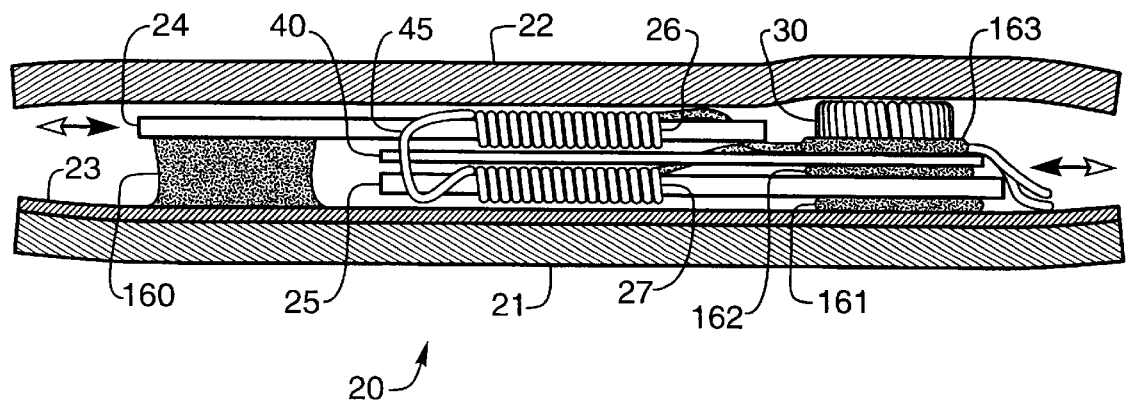
FIG. 4 is aside view of the Respiratory Inductive Plethysmography Band Transducer.

FIGS. 2 and 4 show that magnetic tape 24 is attached at one end thereof to elastic strip 21 at attachment point 60 preferably by a hot melt glue 160. Similarly magnetic tape 25 is attached at one end thereof to elastic strip 21 at attachment point 61 preferably by a hot melt glue 161. The wire windings 26, 27 are proximate each other and separated by insulation plate 40 such that relative movements of the wire windings 26, 27 will mutually induce currents in the windings. The relative movements occur when elastic strip 21 stretches or contracts. Since the wire windings 26, 27 are very close together a large inductance is induced. Further since the relative motion of the wire windings 26, 27 is large, a good modulated signal is produced. Elastic strips 21 and 22 are sewn or otherwise attached at their perimeters to encase the Respiratory Inductive Plethysmography Band Transducer 20. An inelastic strip 23 is sewn or otherwise attached to elastic strip 22 adjacent the magnetic tapes 23, 25 to limit the motion of the elastic strip 22 and so limit the movement of adjacent elastic strip 21 and the maximum displacement of the magnetic tapes 24, 25 relative to each other. The inelastic strip 23 protects the Reparatory Inductive Plethysmography Band Transducer 10 from being damaged due to excessive and abnormal stretching. The inelastic strip 23 does not interfere with the expansion and contraction of the elastic strips 21 and 22 or the relative motion of the wire windings 26, 27 during breathing of the patient.

The insulation plate 40 is held in place by attachment to the magnetic tape 25 at attachment point 62 preferably by applying hot melt glue 162. Similarly toroidal transformer 30 is attached to insulation plate 40 at attachment point 63 preferably by applying hot melt glue 163. The toroidal transformer 30 has wires 28 and 29 for connection to wire windings 26 and 27 respectively. The toroidal transformer 30 also has wires 31, 32 leading out of the Respiratory Inductive Plethysmography Band Transducer Belt 10 to supporting electronics 70 which send and receive signals from the Respiratory Inductive Plethysmography Band Transducer 20. Although a toroidal transformer 30 is shown and described herein any equivalent transformer may be used.

When the Respiratory Inductive Plethysmography Band Transducer Belt 10 is fastened around the chest of a patient it can be preloaded with a tension at a stage of breathing such as exhaling. The elastic strips 21 and 22 will be stretched a little bit or preloaded at this point. When the patient takes a breath his chest will expand and stretch the elastic strips 21 and 22. When the elastic strip 21 stretches or contracts the wire windings 26, 27 will move relative to one another setting up a mutual inductance. When a carrier signal from electronics 70 is applied to toroidal transformer 30 the carrier signal will be transformed and sent to the wire windings 26 and 27 around magnetic tapes 24, 25 by wires 28, 29. The relative movement of the wire windings 26, 27 will modulate the signals and the modulated signals will be transported in reverse thought the same toroidal transformer 30 and wires 31, 32 to be detected by electronics 70 and provide information about the patient's respiration.

Alternatively, if the Respiratory Inductive Plethysmography Band Transducer Belt 10 is stretched a little when it is put on, during a full breath of the patient, then when the patient is exhaling the elastic will contract moving the magnetic tapes 24, 25 relative to each other producing a signal.

The Respiratory Inductive Plethysmography Band Transducer Belt 10 may also be partly preloaded such that it can expand or contract from its initial position.

If the belt is first placed on the patient in a partly preloaded position and the belt shifts on the patient such that the diameter of the belt changes, the position of the wire windings 26 and 27 will move relative to each other. If more wire windings 26, 27 are adjacent after the shift a larger induced signal will be detected, and if fewer wire windings 26, 27 are adjacent after the shift a smaller induced signal will be detected. Since the signal is directly proportional to the diameter of the patient, when the patient inhales his diameter increases and when the patient exhales his diameter decreases. However if the belt shifts to a larger or smaller diameter portion of the chest the signals will change due to the alignment of the wire windings 26, 27. By measuring the midpoint of the amplitude of the inhaling and exhaling signals when the belt is first attached to get a reference point, the monitor can determine if the belt has shifted to a new position by measuring the diameter of the chest at the midpoint of a breath at a later time. If the relative position of the wire windings is known to be totally adjacent before preloading, before the elastic material is stretched, then at the preloaded position wherein the wire windings 26, 27 are offset from being directly adjacent such that if the belt shifts to a lower diameter position the wire windings 26, 27 will be more adjacent, then the amplitude of the middle of the signal will increase indicating a smaller diameter position of the belt on the patient. If compared to the same initial conditions the amplitude of the signal at the midpoint of breathing has decreased the diameter of the belt around the patients chest has increased. By knowing the alignment of the wire windings 26, 27 and the induction occurring for the initial conditions of the belt's diameter, the signals received in electronics 70 can be adjusted for the position of the belt shifting thus providing a constant readout of a signal for monitoring the respiration of a patient as the belt diameter shifts over time.

The electronics of mutually induced currents is well known, as is the modulation of carrier waves and transformers. U.S. Pat. No. 5,131,399 to Sciarra is attached hereto and incorporated herein by reference for showing an example of such known electronics.

Although the application has been drafted with the monitoring of human patients in mind, the device may be used on any animals such as horses, dogs and cat, where the chest cavity expands and contracts while breathing. Similarly the invention can be used to measure the expansion and contraction of any object with a changing diameter or length. The device may for example be used on a bladder to detect leaks, or for the filling or draining of the bladder. The device may also be used as a strain gauge for linear expansions and contractions rather than for diameters expanding and contracting.

Obviously, many modifications and variations of the present invention are possible in light of the above teachings. It is therefore to be understood that, within the scope of the appended claims, the invention may be practiced otherwise than as specifically described.

What is claimed is:

1. An inductive transducer comprising:

an elastic material for attachment to an object, a first magnetic tape having a first wire winding thereon, the first magnetic tape attached to the elastic material, a second magnetic tape having a second wire winding thereon, the second magnetic tape attached to the elastic material, wherein the first wire winding and the second wire winding are proximate each other and electrically connected, such that the when the elastic material expands and contracts there is relative motion between the first and second wire windings, an insulation plate between the first magnetic tape and the second magnetic tape, a toroidal transformer connected to the first and second wire windings, a signal source for sending a carrier signal to the toroidal transformer, such that when the object expands or contracts the relative movement of the first and second wire windings produces a mutual inductance therein and modulates the carrier signals, a signal detector attached to the toroidal transformer for detecting the modulated signals therefrom such that the modulated signals measure the expansion and contraction of the object.

2. An inductive transducer as in claim 1 wherein:

an inelastic belt is attached to the elastic material such that the inelastic belt is fastened around the object to be measured.

3. An inductive transducer as in claim 2 wherein:

the inelastic belt comprises, a first inelastic belt portion attached to the elastic material, and a second inelastic belt portion attached to the elastic material and a fastener means for connecting the first elastic belt portion to the second elastic belt portion.

4. An inductive transducer as in claim 1 wherein:

the object measured is a human torso and the measurement relates to the respiration of the human.

5. An inductive transducer as in claim 1 wherein:

the elastic material comprises a first piece of elastic material with the first and second magnetic tapes attached thereto, the insulation plate secured therebetween and the toroidal transformer attached to the insulation plate, and a second piece of elastic material for sandwiching the first and second magnetic tapes, the insulation plate and the toroidal transformer between the first and second pieces of elastic material.

6. An inductive transducer as in claim 5 wherein:

a strip of inelastic material attached to the second piece of elastic material proximate the first and second magnetic tapes limits the relative motion of magnetic tapes.

7. An inductive transducer as in claim 6 wherein:

an inelastic belt is attached to the elastic material such that the inelastic belt is fastened around the object to be measured.

8. An inductive transducer as in claim 7 wherein:

the inelastic belt comprises, a first inelastic belt portion attached to the elastic material, and a second inelastic belt portion attached to the elastic material and a fastener means for connecting the first elastic belt portion to the second elastic belt portion.

9. An inductive transducer as in claim 8 wherein:

the object measured is a human torso and the measurement relates to the respiration of the human.

10. An inductive transducer as in claim 1 wherein:

the elastic material is preloaded to separate the first wire winding and the second wire winding to reduce the mutual inductance therebetween, the signal detector notes the midpoint of the initial respiration amplitudes to determine the diameter of the object at the initial inductance settings, and compensates for belt slippage on the object to different diameters by measuring the midpoint of the respiration amplitudes at a later time and adjusting the output signals accordingly.

* * * * *

UNITED STATES PATENT AND TRADEMARK OFFICE
CERTIFICATE OF CORRECTION

PATENT NO. : 6,142,953
DATED : November 7, 2000
INVENTOR(S) : David Burton and Jiang Hong Tan Page 1 of 1

It is certified that error appears in the above-identified patent and that said Letters Patent is hereby corrected as shown below:

<u>Column 5:</u>
Line 3 after "that" delete "the"

Signed and Sealed this

Twelfth Day of June, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,142,953
DATED : November 7, 2000
INVENTOR(S) : David Burton and Jiang Hong Tan It is certified that error appears in the above-identified patent and that said Letters Patent is hereby corrected as shown below:

<u>Column 5:</u>
Line 3 after "that" delete "the"

Signed and Sealed this

Twenty-sixth Day of June, 2001

*Attest:*

*Attesting Officer*

NICHOLAS P. GODICI
*Acting Director of the United States Patent and Trademark Office*